(12) United States Patent
Scott

(10) Patent No.: US 6,398,933 B1
(45) Date of Patent: Jun. 4, 2002

(54) TWO DIMENSIONAL GEL ELECTOROPHORESIS SYSTEM

(75) Inventor: Charles B. Scott, Rancho Santa Fe, CA (US)

(73) Assignee: C.B.S. Scientific Co., Inc., Rancho Santa Fe, CA (US)

(*) Notice: Subject to any disclaimer, the term of this patent is extended or adjusted under 35 U.S.C. 154(b) by 0 days.

(21) Appl. No.: 09/386,768

(22) Filed: Aug. 31, 1999

Related U.S. Application Data
(60) Provisional application No. 60/098,408, filed on Aug. 31, 1998.

(51) Int. Cl.[7] ............................................. G01N 27/26
(52) U.S. Cl. ...................... 204/466; 204/618; 204/616; 204/467
(58) Field of Search ................. 204/456, 457, 204/459, 466, 467, 606, 608, 610

(56) References Cited

U.S. PATENT DOCUMENTS

| | | | | |
|---|---|---|---|---|
| 4,693,804 A | * | 9/1987 | Serwer | 204/466 |
| 5,071,531 A | * | 12/1991 | Soane | 204/616 |
| 5,407,546 A | * | 4/1995 | Schickle | 204/459 |
| 6,036,831 A | * | 3/2000 | Bishop | 204/618 |
| 6,187,250 B1 | * | 2/2001 | Champagne | 264/495 |

FOREIGN PATENT DOCUMENTS

| | | | |
|---|---|---|---|
| DE | 3232685 A1 | * | 3/1984 |
| JP | 61235599 A | * | 4/1985 |
| WO | WO-9411730 A1 | * | 5/1994 |

OTHER PUBLICATIONS

Derwent abstracts of Westermeir (DE 3232685 A1) Mar. 15, 1984.*

Derwent abstract of Usuda (JP 61235599 A) Apr. 11, 1985.*

* cited by examiner

Primary Examiner—T. Tung
Assistant Examiner—Alex Noguerola
(74) Attorney, Agent, or Firm—James C. Weseman, Esq.; The Law Offices of James C.Weseman

(57) ABSTRACT

System, method and apparatus for two dimensional gel electrophoresis performed in a unified manner which includes the performance of two fragment separations in a single gel without intermediate physical manipulation.

12 Claims, 5 Drawing Sheets

TWO DIMENSIONAL GEL ELECTOROPHORESIS SYSTEM

This appl. claims priority from provisional appl. Ser. No. 60/098408, filed Aug. 31, 1998.

TECHNICAL FIELD

The present invention relates to the field of electrophoretic separation of molecules, and, more particularly, to two-dimensional electrophoretic separations.

BACKGROUND OF THE INVENTION

Electrophoresis is the process of separating molecules on the basis of the molecule's migration through a gel in an applied electric field. In an electric field, a molecule will migrate towards the pole (cathode or anode) that carries a charge opposite to the net charge carried by the molecule. This net charge depends in part on the pH of the medium in which the molecule is migrating.

One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by both molecular size and isoelectric point.

Thus, electrophoresis in a polymeric gel can also be used to separate molecules, such as RNA and DNA molecules, which all have the same isoelectric point. These groups of molecules will migrate through an electric field across a polymeric gel on the basis of molecular size. Molecules with different isoelectric points, such as proteins, can be denatured in a solution of detergent, such as sodium dodecyl sulfate (SDS). The SDS-covered proteins will have similar isoelectric points and will migrate through the gel on the basis of molecular size. The separation of DNA molecules on the basis of their molecular size is an important step in determining the nucleotide sequence of a DNA molecule.

A polymeric gel electrophoresis system is typically set up in the following way: A gel-forming solution is allowed to polymerize between two glass plates that are held apart on two sides by spacers. These spacers determine the thickness of the gel. Typically, sample wells are formed by inserting a comb-shaped mold into the liquid between the glass plates at one end and allowing the liquid to polymerize around the mold. Alternatively, the gel may be cast with a flat top and a pointed comb inserted between the plates so that the points are slightly imbedded in the gel. Small, fluid-tight areas between the points can be filled with a sample.

The top and bottom of the polymerized gel are placed in electrical contact with two separate buffer reservoirs. Macro-molecule samples are loaded into the sample wells via a sample-loading implement, such as a pipette, which is inserted between the two glass plates and the sample is injected into the well. To prevent sample mixing, it is advantageous to inject-the sample as close to the gel as possible. It is difficult to place the tip of the pipette or loading implement close to the gel because the pipette tip is often wider than the gel.

An electric field is set up across the gel, and the molecules begin to move into the gel and separate according to their size. The size-sorted molecules can be visualized in several ways. After electrophoresis, the gels can be bathed in a nucleotide-specific or protein-specific stain which renders the groups of size-sorted molecules visible to the eye. For greater resolution, the molecules can be radioactively labeled and the gel exposed to X-ray film. The developed X-ray film will indicate the migration positions of the labeled molecules.

Both vertical and horizontal assemblies are routinely used in gel electrophoresis. In a vertical apparatus, the sample wells are formed in the same plane as the gel and are loaded vertically. A horizontal gel will generally be open on its upper surface, and the sample wells are formed normal to the plane of the gel and also loaded vertically.

Two-dimensional electrophoresis is a useful technique for separating complex mixtures of molecules, often providing a much higher resolving power than that obtainable in one-dimension separations. The technique permits component mixtures of molecules to be separated according to two different sets of properties in succession, and lends itself to a variety of different combinations of separation parameters. One combination is separation based on charge followed by separation based on molecular weight, as discussed separately above. Another is separation in a gel of one concentration followed by separation in a gel of the same material but of another concentration. Two-dimensional separations have also been used to create a stepwise change in pH, to separate first in a homogeneous gel and then in a pore gradient gel, to separate in media containing first one molecule solubilizer and then another, or in media containing a solubilizer first at one concentration and then at another concentration, to separate first in a discontinuous buffer system and then in a continuous buffer system, and to separate first by isoelectric focusing and then by homogeneous or pore gradient electrophoresis. Combinations such as these can be used to separate many kinds of molecular components, including serum or cell proteins, bacterial proteins, non-histone chromatin proteins, ribosomal proteins, mixtures of ribonucleoproteins and ribosomal proteins, and nucleic acids.

The first dimension of a two-dimensional electrophoresis system is typically performed in an elongate rod-shaped gel having a diameter in the vicinity of 1.0 mm, with migration and separation occurring along the length of the rod. Once the solutes have been grouped into individual zones along the rod, the rod is placed along one edge of a slab gel and the electric current is imposed across the rod and slab in a direction perpendicular or otherwise transverse to the axis of the rod. This causes the migration of solutes from each zone of the rod into the slab gel, and the separation of solutes within each zone.

Difficulties in two-dimensional electrophoresis arise in the handling of the rod-shaped gel after the first dimension separation has occurred and in placing the gel in contact with the slab gel to prepare for the second dimension separation. The first dimension separation is generally performed while the rod gel is still in the tube in which it was cast. Once the separation in the tube has been performed, the rod is physically removed from the tube, then placed along the exposed edge of the slab gel. The extraction of the rod from the tube and the act of placing it along the slab gel edge require delicate handling, and even with the exercise of great care, the gel is often damaged and the solute zones are distorted or disturbed. Alignment and full contact of the rod with the slab gel are important for achieving both electrical continuity and unobstructed solute migration between the gels. Furthermore, considerable time is involved in the handling and placement of the rod, and errors can result in loss of data. Gel strips can be used as alternatives to the rod, but are susceptible to similar difficulties, opportunities for error, and a lack of reproducibility.

Many of these problems are eliminated by gel packages that contain both the elongated first dimension gel and the slab-shaped second dimension gel in a common planar arrangement that permits the two separations to be done in succession without any intervening insertion or removal of either gel. One such arrangement and method of use is disclosed in U.S. Pat. No. 4,874,490.

More recently, a new pre-cast gel structure and method has been described in U.S. Pat. No. 5,773,645, which describes a combined water-swellable strip gel and a slab gel on a common support for two-dimensional electrophoresis. In this disclosure, the strip gel is isolated from the slab gel by a fluid-impermeable and electrically insulting barrier. The first dimension separation is performed by placing the liquid sample and buffer in the reservoir to cause the gel to swell and to load it with sample, and then passing an electric current through the reservoir. The barrier, which is joined to the support in an easily breakable manner, is then removed, and the strip gel is placed in contact with the slab gel for the second dimension separation..

In each case, each dimension of the two dimensional electrophoresis is performed in a physically separate gel. When the second dimension is run, the physical discontinuity of the separate gels give rise to a lack of resolution, as well as the need to carefully manipulate the gel during the course of the protocol.

Thus, it would be desirable to provide a gel system and apparatus which would allow the separation of molecules in two dimensions, relying on two separate parameters, within the same gel and not requiring a manipulation or discontinuity to establish and maintain high resolution in each dimension.

An automated system which performs the two dimensional gel electrophoresis in a single gel has been described in PCT Publication WO 96/39625 which utilizes computer controlled robotics to physically rotate the gel slab 90 degrees after the first dimension gel separation has been performed.

An electrophoresis device which eliminates the requirement to physically rotate the gel slab 90 degrees after the first dimension gel separation has been described in U.S. Pat. No. 5,562,813. The device includes an electrophoresis medium enclosed between two plates positioned in contact with a first pair and a second pair of compartments for electrophoresis liquid. Each of the compartments is provided with electrodes to make electrophoretic contact on either side and mutually transversely of each other with the electrophoresis medium, and the compartments are disposed and adapted such that the electrophoresis unit assumes a standing position in the apparatus.

However, each of the known prior art devices includes limitations or unneeded complexities, as will hereinafter be more readily apparent.

DISCLOSURE OF THE INVENTION

The present invention provides a system for performing two dimensional gel electrophoresis. In one aspect, the invention provides a unified system comprising a means for electrophoretically separating the components of a sample in a slab gel sample well along a first separation path having an axial dimension and a longitudinal dimension extending from the sample well generally along a first dimension in the slab gel. In the same system, a second means is provided for electrophoretically separating the primarily separated sample components in a second dimension by utilizing a second separation path having an axial dimension and a longitudinal dimension extending from the first separation path generally along a second dimension in the slab gel.

While in certain embodiments a slab gel is integrally formed to provide both separation paths, other embodiments are contemplated where, for example, a narrower strip of gel, or stacker, is formed along one edge of the primary slab gel to provide a medium for the first separation path.

A further aspect of the invention provides a method for separating a sample into molecular components by utilizing two-dimensional gel electrophoresis comprising providing a two-dimensional gel electrophoresis system as disclosed, loading a sample into the sample well, imposing an electrical field constrained generally along the first sample path to effect electrophoretic separation of the components of the sample along the first sample path, and imposing an electrical field generally along the second sample path to effect electrophoretic separation of the primarily separated components of the sample along the second sample path.

A still further aspect of the invention provides an apparatus for practicing various aspects of the invention in selected embodiments.

DETAILED DESCRIPTION OF THE INVENTION

Figure 1:
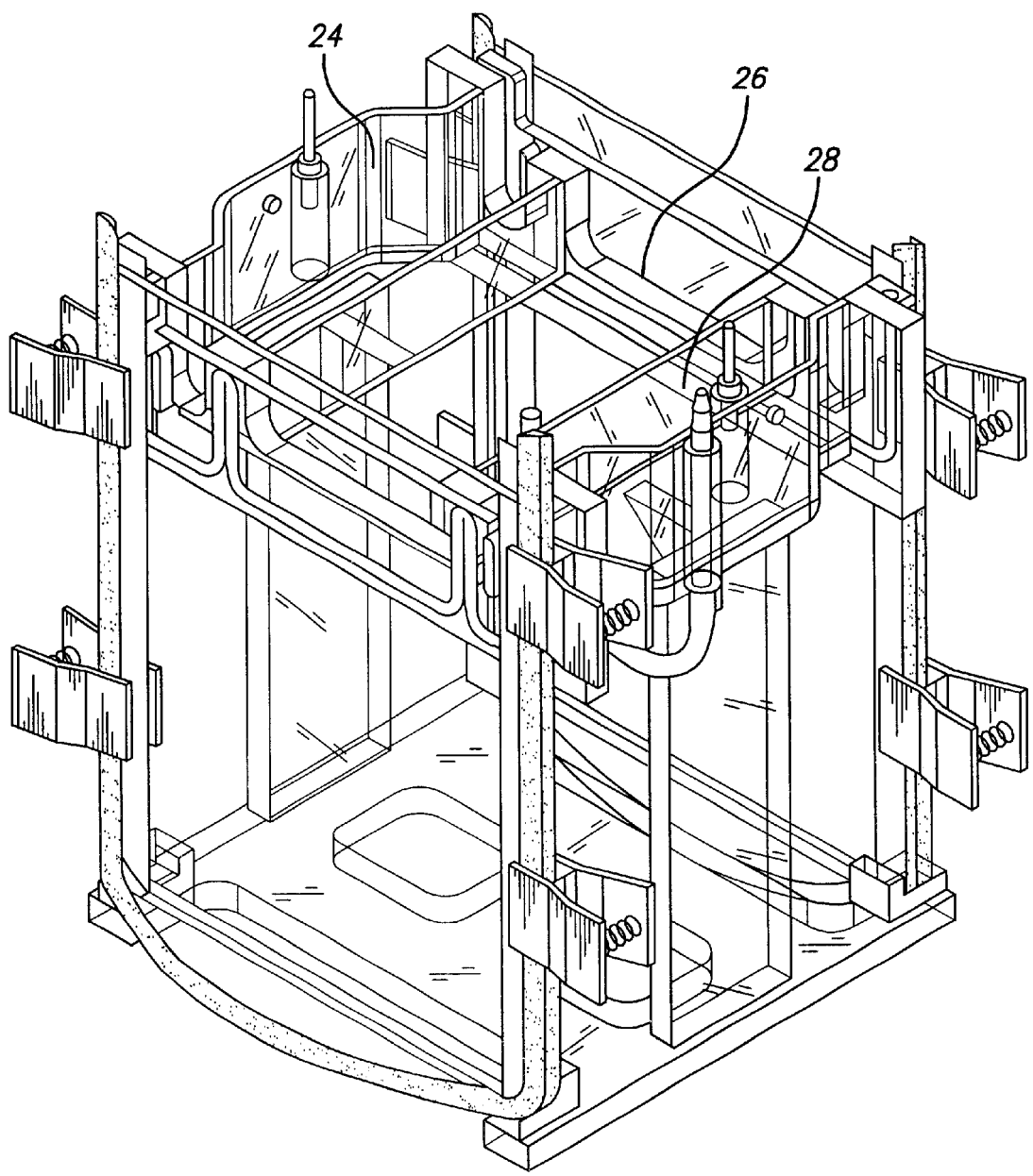
FIG. 1 is a perspective view of a complete assembly of one embodiment of the present invention.

The present invention provides a system for performing two dimensional gel electrophoresis. In one aspect, the invention provides a system comprising a means for electrophoretically separating the components of a sample in a slab gel sample well along a first separation path having an axial dimension and a longitudinal dimension extending from the sample well generally along a first dimension in the slab gel. In the same system, a second means is provided for electrophoretically separating the primarily separated sample components in a second dimension by utilizing a second separation path having an axial dimension and a longitudinal dimension extending from the first separation path generally along a second dimension in the slab gel. The samples to be separated and analyzed in accordance with the present invention will comprise any samples of molecular components susceptible to such separation and analysis, commonly biologically-derived molecular components and most often comprising components of either nucleic acids or proteins, or mixtures thereof.

While in certain embodiments a slab gel is integrally formed to provide both separation paths, other embodiments are contemplated where, for example, a narrower strip of gel, or stacker, is formed along one edge of the primary slab gel to provide a medium for the first separation path.

A further aspect of the invention provides a method for separating a sample into molecular components by utilizing two-dimensional gel electrophoresis comprising providing a two-dimensional gel electrophoresis system as disclosed, loading a sample into the sample well, imposing an electrical field constrained generally along the first sample path to effect electrophoretic separation of the components of the sample along the first sample path, and imposing an electrical field generally along the second sample path to effect electrophoretic separation of the primarily separated components of the sample along the second sample path.

A still further aspect of the invention provides an apparatus for practicing various aspects of the invention in selected embodiments. Each aspect of the invention will be described as necessary in order to provide a complete description of the invention.

One unique feature of the invention is that it provides the means to perform two dimensional gel electrophoresis in a single gel without requiring physical manipulation of the gel during the course of the procedure.

Although certain embodiments of the invention will be described with reference to an apparatus which resembles a conventional "vertical" slab gel device, it will readily be appreciated that the apparatus of this embodiment actually combines aspects of a "horizontal" gel device integrated with such a "vertical" device.

In order to establish a background, a vertical slab gel device should be understood in general terms. The various components of such a device generally include a support framework with an upper electrolyte or buffer reservoir, a pair of apposing plates, typically glass plates, into which a gel has been cast, and a container, or tank, into which the device is placed, and which serves as the second reservoir. The gap between the two plates is set by a pair of spacers positioned along the lateral edges of the plates, and the slab gel occupies a portion of the gap. The plates and spacers will either be of unitary construction formed by molding or welding, or held together by clamps of conventional construction well known to those skilled in the manufacture or use of slab gels and cassettes.

The inner-most of the two plates, that is the one which is clamped adjacent the support framework, will have a notch which is matched to a similar opening in the upper buffer reservoir, so that when the upper reservoir is filled, electrolyte will spill through the notch and onto the upper surface of the gel. An electrode will be provided in the upper reservoir, so that a charge can be imposed on the upper surface of the gel via the electrolyte. The lower edge of the vertical slab gel is likewise exposed, and when the device is placed in the tank, and the tank partially filled with electrolyte sufficient to contact the lower edge of the gel, the activation of the second electrode provided in the lower reservoir (with opposite polarity to the upper electrode) will cause the establishment of an electrical field with a current flowing through the gel between the upper and lower edges. In this manner, electrophoretic separation of the sample components is effected as the components are exposed to the electrophoretic separation parameters established in the gel. These parameters can be physical, such as the concentration or density of the gel matrix, or the temperature of the gel matrix, such as when a temperature gradient is established from one region of the gel to the next. Typically, such a temperature gradient will be established using a series of thermal conducting cells, located adjacent to at least one of the glass plates. Each cell will include a source of thermal control, typically a heating element, and a thermal measuring device, typically a thermistor, the combination of which will generally be under the control of a programmable temperature gradient control system, for example a computer controlled system. The temperature control element will be set to operate at a predetermined temperature, and will be maintained at approximately the preset temperature, by the computer control operating on the information provided by the thermal measuring device. This arrangement allows virtually any desired temperature gradient to be established and maintained during the electrophoretic separation performed in accordance with the present system.

Alternatively, or additionally, the chemical parameters of the gel can be varied, such as the pH of the gel, or the inclusion of, for example, denaturing agents which will denature certain of the components of the sample. Often, the denaturing agents will be included in the gel in a concentration gradient from one region of the gel to the next. Such gradients will generally be established during the casting of the gel, for example by gradient mixing devices in accordance with means well known in the art.

Figure 2:
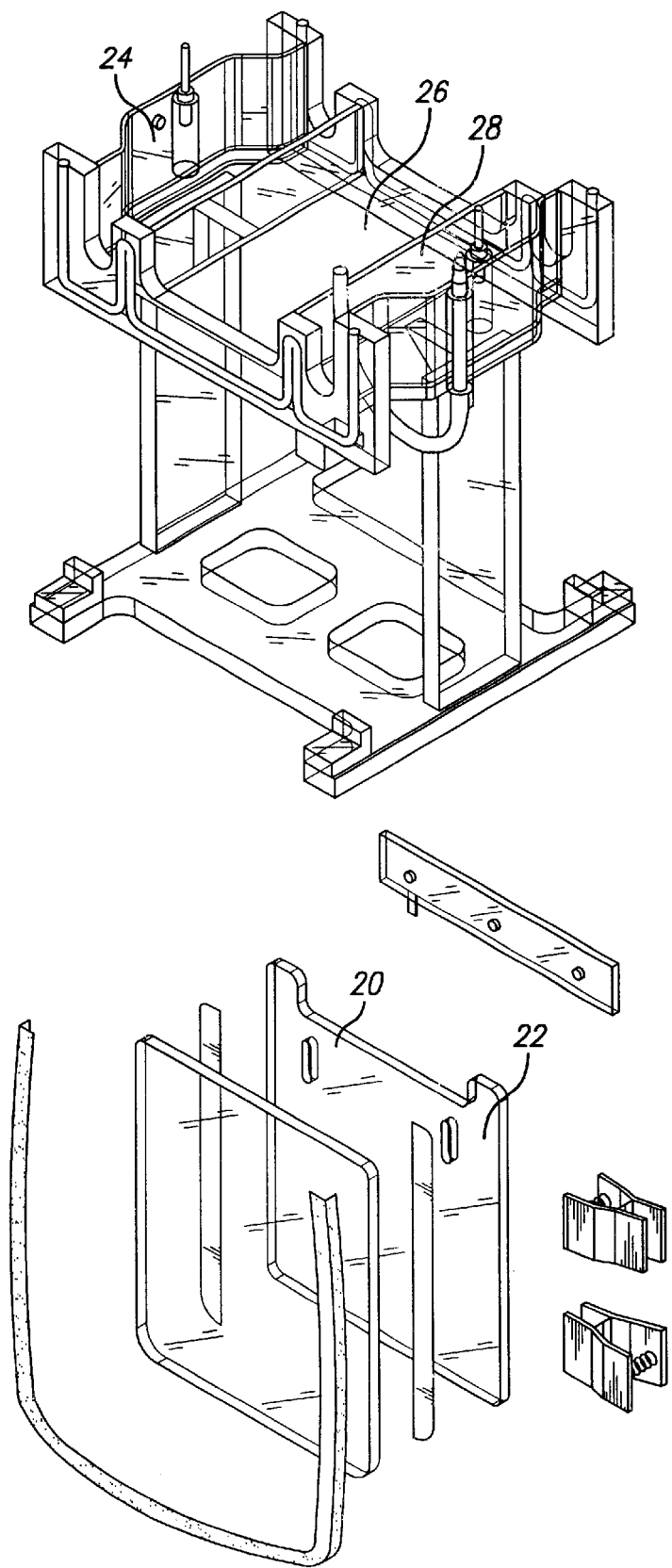
FIG. 2 is an exploded perspective view selected components of the assembly of FIG. 1.

In the practice of the present invention, embodiments as depicted in FIGS. 1 and 2, which generally resemble the configuration of a vertical slab gel apparatus as described above, will generally utilize the axis from the upper reservoir to the lower reservoir as one separation path for the sample under analysis. In numerous embodiments of the invention, where the two dimensional separations are conducted separately, this separation path will constitute the second dimension. In many such embodiments, the gradients in, e.g., temperature or denaturing agent concentration will be established along this separation path.

Also in many such embodiments, the first separation path, defining thereby the first dimension, will generally be established in the upper portion of the gel slab. In such embodiments, the sample will be loaded into a single sample well, formed for example with a single tooth comb, in the upper edge of the slab gel. The present system then further provides a mean for imposing an electrical field from proximate one edge of the gel and extending horizontally through the sample well and extending to a region proximate the opposite edge of the gel. This feature of the present system enables the sample to be separated along this first separation path in a manner similar to horizontal gel electrophoresis, and subject to the physical and chemical electrophoretic parameters established in the slab gel.

Figure 4:
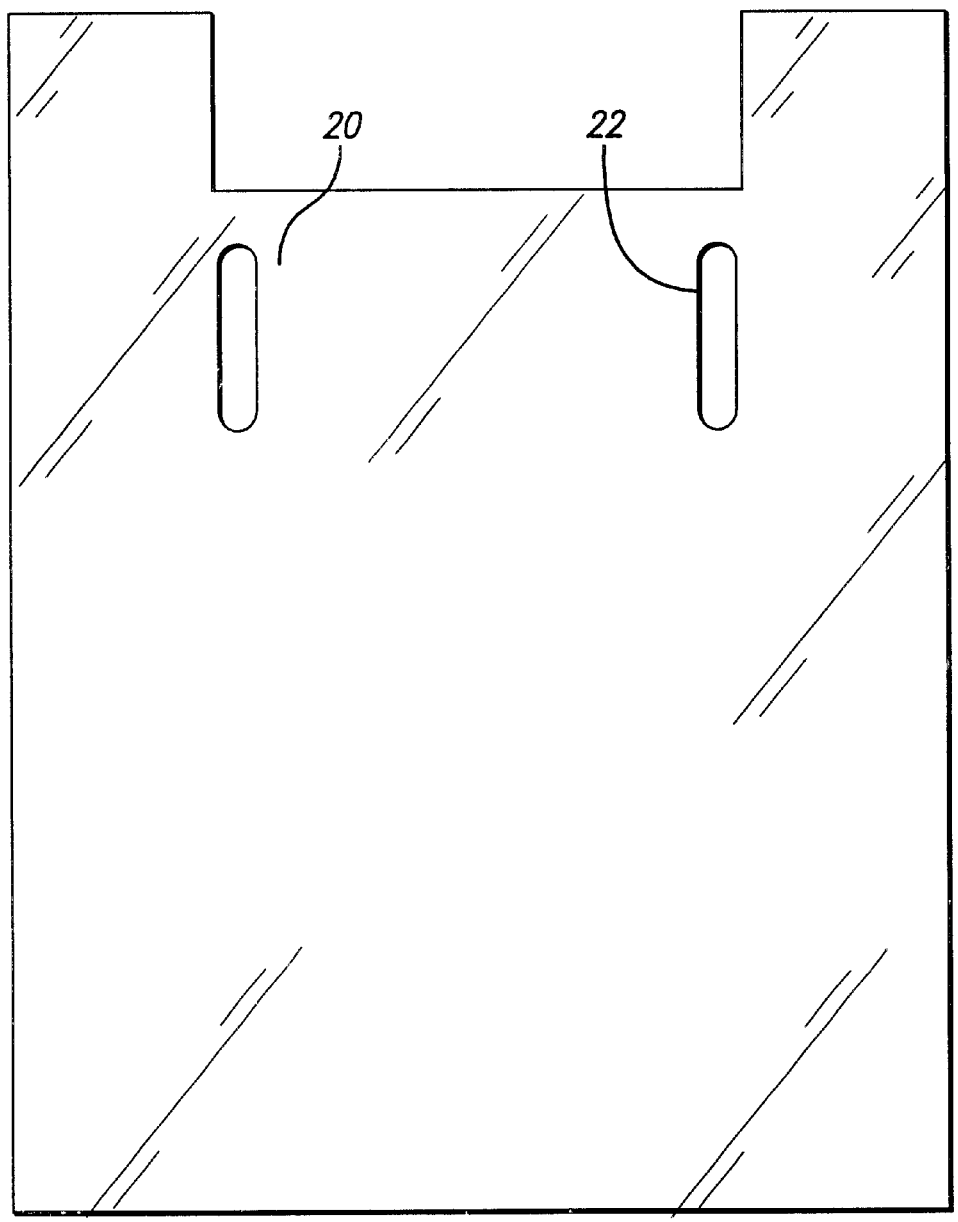
FIG. 4 is a horizontal front elevation view of one of the glass plate components of the assembly of FIG. 1.

One aspect of the present invention which differs from conventional electrophoresis practice is the means for imposing this first, "horizontal" separation path. Such means can include providing electrodes which penetrate into the slab gel to define the first separation path. Such electrodes can penetrate, for example, through the spacers which define the edges of the gel slab, or through one or both of the glass plates which form the gel chamber. Alternatively, the present invention provides for the inclusion of a plurality of channels 20, 22 through, for example, the rear, or notched, plate, as depicted in FIGS. 2 and 4. Such channels provide a means to allow current flow through a constrained portion of the gel in a horizontal direction to define the first separation path, when combined with other unique aspects of the invention. This feature provides a basic component of the present system by providing a means for electrophoresing a sample along the first separation path by providing a means for directing an electrical field into a narrow region of the gel and constraining the field in such a way so as to separate the components of the sample along a narrow separation path, roughly analogous to a horizontal tube gel portion of the slab gel.

Figure 3A:
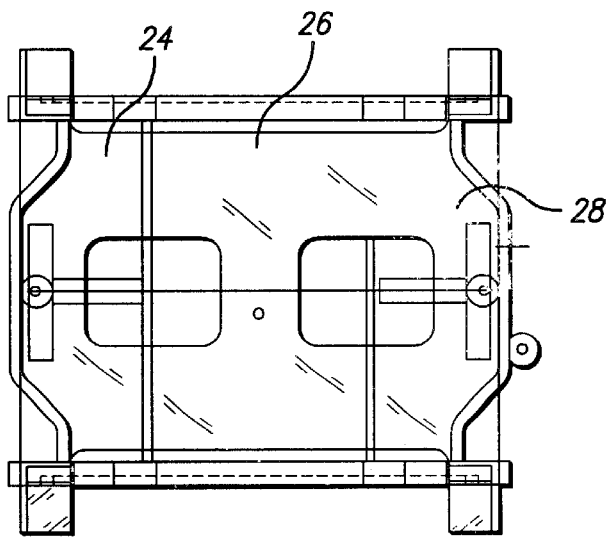
FIG. 3 presents a horizontal front elevation, a side elevation and a top plan view of the electrophoresis support component of the assembly of FIG. 1.
Figure 3B:
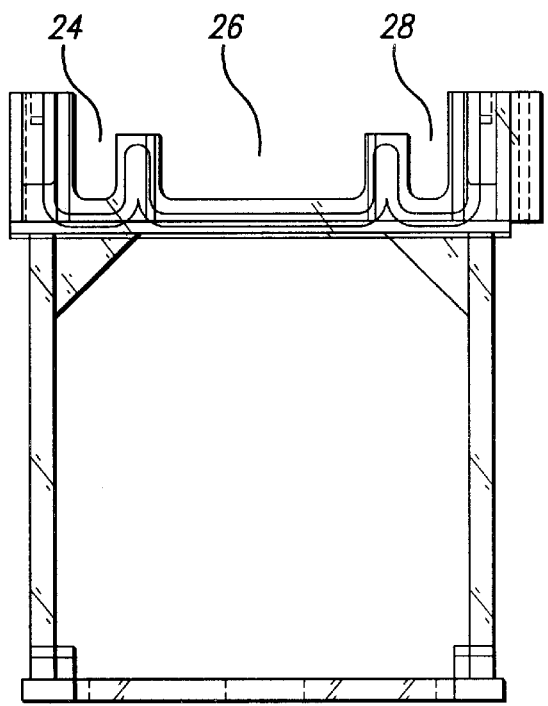
Figure 3C:
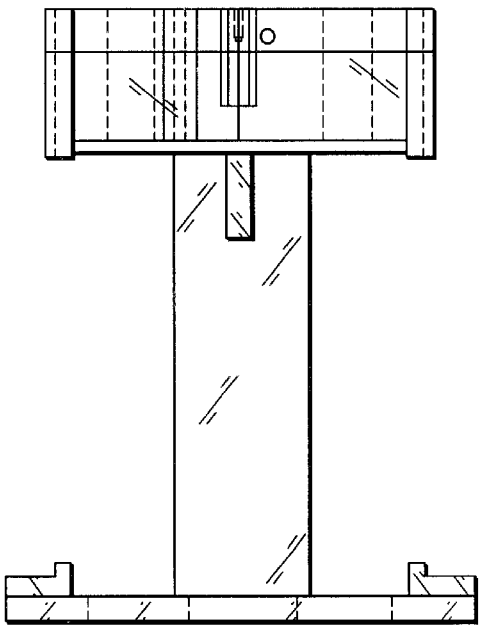

A further unique feature of the invention, working in cooperation with the plurality of channels, is the provision of separate chambers 24, 26, 28 in the upper electrolyte reservoir, and separate electrodes, as depicted in FIGS. 2 and 3, so that the upper reservoir can be utilized as a "horizontal" device in conjunction with the channels of the notched plate to impose a first electrical field constrained along a first separation path, i.e. "horizontally" along a path generally parallel to the upper edge of the gel. An embodiment providing this feature will divide the upper reservoir into distinct chambers aligned generally along the upper edge of the gel, as shown in FIGS. 1 and 3. The outermost chambers will be configured so that, when filled to a preselected level with electrolyte, they will provide electrolyte access to the channels in the notched plate, but prevent contact with the upper edge of the gel. Each of such chambers will be provided with an independent electrode, so that when activated, a current can flow from one chamber, through the appropriate channel, through the region of gel adjacent to the channel and extending to the other channel, and finally to the oppositely charged electrode.

Having arranged such a device, a single sample well can be established in the upper edge of the gel, positioned adjacent to the first electrolyte channel. By loading a sample of molecular components into the well, establishing electrolyte into each end chamber to the appropriate level, and activating the electrodes, the electrical field established along the separation path, extending longitudinally from the first channel to the second, will cause the electrophoretic separation of the sample components along this path. The cross sectional area of the first separation path will then be determined by the size of the sample, and the constraint on the electrical field imposed by the electrolyte channels, as the current would flow along the linear path of least resistance. The longitudinal axis of the first separation path would be defined by the distance between the channels, and the amount of time the electrophoresis is performed.

In conventional practice, a slab gel will be cast between the two plates, or as a part of a pre-made cassette. In a gradient gel, the gradient is generally established vertically so that along any horizontal cross section, the gel concentrations will be substantially equal. Thus, a sample subject to electrophoretic separation along the first separation path will experience approximately uniform conditions, and the separation will be generally in accordance with the length or molecular weight of the various components. Clearly, however, a gel can be cast in a manner which presents a variety of conditions to such a horizontal separation path, without exceeding the scope of the present invention.

One additional embodiment of such a gradient system would be to cast the gradient portion of the slab gel up to the channels, and then cast a uniform gel, analogous to a stacker gel, on top of the slab gel. The first separation path would occupy a portion of this uniform gel, and the size separation could thereby be more tightly regulated.

Once the molecular components of the sample are primarily separated along the first separation path, the electric field would be interrupted, and electrolyte would be brought into contact with the upper edge of the gel. This could be done by filling the chambers further, so that the electrical separation is removed, or by maintaining an additional chamber for such a purpose. Then, by activating the upper electrode (s) with identical polarity, and activating the electrode in the lower reservoir with opposite polarity, an electrical field would be imposed on the gel transverse to the original field, that is from upper edge to lower edge of the slab gel, causing a electrophoretic migration in the second dimension. In the case of a denaturant gradient gel, the components of the sample would experience ever increasing concentrations of denaturant, and the separation of components of similar length or weight would be subject to a new separation parameter. In this second separation path, the axial cross section of the path would be defined by the longitudinal dimension of the first separation path, and the longitudinal dimension would be approximately defined by the dimension from the upper edge to the lower edge of the gel, and by the amount of time the electrophoresis is performed.

Methods for Performing Two Dimensional Electrophoresis

There are many formats currently known for performing two dimensional gel electrophoresis, which permit mixtures of molecules to be separated based upon a variety of different combinations of separation parameters. One such combination utilizes separation based on charge and on molecular weight, in either order. Another is separation in a gel of one concentration followed by separation in a gel of the same material but of another concentration. Two-dimensional separations have also been used to create a stepwise change in pH, to separate first in a homogeneous gel and then in a pore gradient gel, to separate in media containing first one molecule solubilizer and then another, or in media containing a solubilizer first at one concentration and then at another concentration, to separate first in a discontinuous buffer system and then in a continuous buffer system, and to separate first by isoelectric focusing and then by homogeneous or pore gradient electrophoresis. Combinations such as these can be used to separate many kinds of molecular components, including serum or cell proteins, bacterial proteins, non-histone chromatin proteins, ribosomal proteins, mixtures of ribonucleoproteins and ribosomal proteins, and nucleic acids.

In nucleic acids, two dimensional systems have been developed to separate nucleic acid fragments in one dimension based upon their length (and, proportionately, by molecular weight), and in the other dimension on the basis of their base pair sequence (more specifically, for DNA the separation will be based on the relative content of G-C pairs versus A-T pairs). One example of such a two dimensional technique is described in U.S. Pat. No. 5,068,176, the entire content of which is incorporated herein by this reference. In such an analysis, the nucleic acid fragments generated are first separated on the basis of their length in a neutral polyacrylamide gel, and subsequently, in the second dimension, are separated on the basis of their base pair sequence in a polyacrylamide gel having an increasing concentration gradient of a nucleic acid denaturant parallel to the direction of electrophoresis.

Analyses such as are disclosed therein include the general steps of DNA isolation and restriction enzyme digestion, followed by gel electrophoretic separation. Thereafter, the gel will generally be stained to visualize the separation pattern, the pattern will be transferred to a medium for hybridization with a probe, and the hybridization pattern analyzed for interpretation of results.

Exemplary of such an analysis is as follows:

DNA Isolation and Restriction Enzyme Digestion

For making 2-D separation patterns as described above, in principle any tissue or cells can be used as a source for the DNA, and subject to standard DNA isolation procedures for providing samples containing molecular components. For example, DNA can be isolated from blood or tissue from different individuals, such as brain tissue in accordance with the following procedure: Deep frozen postmortem cerebellum is fragmented and incubated overnight at 65° C. in 2 volumes of a solution containing 100 mM Tris, pH 7.5, 250 mM Na-EDTA, 1% sodium dodecyl sulphate (SDS) and 100 µg/mL proteinase K (BRL). After the admixture of 1 volume of 8M potassium acetate, the solution is kept on ice for 2 hours and then extracted with 1 volume of chloroform. The DNA obtained from the aqueous phase by ethanol precipitation is then dissolved in water. The DNA will then be subject to digestion by restriction enzymes, such as endonuclease HaeIII or HinfI (BRL) under conditions as described by the manufacturer.

Electrophoretic Separation

Two-dimensional separation of DNA restriction fragments (e.g. sample size of approximately 10 µg) will be typically carried out in approximately 6% polyacrylamide gels (acrylamide:bisacrylamide, approximately 37:1) poured with a denaturation gradient, which contains, for example, a 10–75% linear concentration gradient of denaturant (where 100% denaturant=7.0M urea, 40% formamide) established parallel to the direction of electrophoresis for the second separation path. These gels are cast by mixing the boundary solutions in a linear gradient former, using a peristaltic pump.

The separation along the first separation path will be performed in the upper region of the gel by applying negative polarization to the electrode in the chamber of the first reservoir which communicates to the gel region proximal to the sample well and applying positive polarization to the electrode in the chamber of the first reservoir which communicates to the gel region at the end of the first separation path distal to the sample well. The separation will be performed at approximately 50–60° C. for 2 hours at 200–250 V in 0.5–1×TAE (1×TAE=40 mM Tris, pH 7.4, 20 mM sodium acetate, 1 mM sodium EDTA). The first dimension separation patterns may, if desired, be visualized by means of staining. However, in order to preserve the integrity of the gel, and the benefits of efficiency in establishing a two dimensional gel separation pattern, a typical operation will ordinarily forego such visualization.

The separated molecular components in the first separation path region will then be subject to a second electrical field applied approximately transversely to the first separation path. In this regard, the first electrolyte reservoir is supplemented with additional electrolyte so as to contact substantially the entire first edge of the slab gel in the region proximal to the first separation path, and all electrodes in the first electrolyte reservoir are subject to negative polarization. Positive polarization is then applied to the electrode in the second electrolyte reservoir which communicates to the gel region distal to the region defining the first separation path. Electrophoresis across a denaturing gradient slab gel is then perform in a manner analogous to conventional DGGE protocols. After electrophoresis for 12 hours at 200–225 V and at 50–60° C., the gel will be stained (in the dark) with ethidium bromide (0.1 µg/ml) for 10 minutes, followed by destaining in deionized water for at least 30 minutes, to visualize the separation pattern.

As an alternative, the electrophoretic separations performed in accordance with the present invention can be performed simultaneously, for example by appropriate selection and simultaneous activation of the electrodes, so that the separation paths are established simultaneously. While the actual track of each separate molecular component of the sample would be expected to differ from the track followed when the separation paths are established separately, the final position of each component, as well as the overall sample two-dimensional separation pattern, will be expected to be substantially identical.

The two-dimensional separation patterns obtained in accordance with the invention are generally analyzed in accordance with various known techniques. For example, the separation patterns are subject to hybridization with labeled probes, then analyzed for hybridization patterns, generally as follows:

1. Transfer of the Separation Pattern to Membrane Filters

For example, the separation patterns are first fragmented by irradiating the gel with 302 nm ultraviolet light (UV) for 4 minutes. Prior to the transfer, the gel is boiled for 5 minutes in 1×TBE (89 mM Tris, 89 mM boric acid, 2 mM sodium EDTA) and then transferred to 1×TBE. Transfer to nylon membranes (Nytran 13N, Schleicher and Schuell or Zetabind, BioRad) is accomplished by electroblotting at 400 mA (12–28 V) at 15° C. in an electroblotting apparatus using graphite plates. Electroblotting is effected over two periods of 45 minutes between 10 sheets of Whatman 3MM paper soaked in fresh 1×TBE (changed between the two electroblotting periods). After transfer, the filter is rinsed in 2×SSC (1×SSC=150 mM NaCl, 15 mM sodium citrate), dried in the air, heated at 80° C. in a furnace for 1 hour, and irradiated with 302 nm UV for 45 seconds.

2. Preparation and Radioactive Labeling of the Probe

The probe is prepared by individually kinating two partially complementary and overlapping oligonucleotides. One such pair represents a core sequence of the nucleic acid molecules under analysis. After kination, the two oligonucleotides are mixed and annealed at 57° C. for 1 hour, followed by ligation by standard procedures (Maniatis et al., 1982). 50 ng of the ligation products are then labeled with $\alpha$ $^{32}$P-dCTP, either by means of the random primed oligo labeling method (Boehringer) or by selfpriming after boiling for 5 minutes and reannealing in the presence of 1 unit of Klenow enzyme (Boehringer), 2 µM dNTP, 50 mM Tris, pH 7.2, 10 mM $MgCl_2$.

3. Hybridization Analysis

The filter is prehybridized in 5×SSC, 20 mM sodium phosphate, pH 7.2, 1% SDS, 1 mM sodium EDTA, 50 µg/mL heparin at 65° C. for 2 hours. After the addition of the denatured probe in a concentration of $1 \times 10^6$ cpm./mL, hybridization will follow at 65° C. for 12 hours. The filter is then washed in 2.5×SSC, 0.1% SDS, thrice at room temperature for 5 minutes and thrice at 65° C. for 20 minutes. Autoradiography will be performed at −80° C. with Kodak XAR-5 film between fine intensifying screens (Kodak) for 12–48 hours.

Alternatively, the two-dimensional separation patterns can be analyzed in accordance with various known automated techniques, generally as follows: The various components of the sample to be analyzed may be labeled with fluorescent markers, which can be detected optically and analyzed. The flourescent markers will be activated by excitation with illumination by a selected wavelength, generated typically by a laser or other source and a filter which allows only the selected wavelength to reach the marker. The resultant emissions will then be passed through a separate filter, to eliminate the excitation frequency, and the results analyzed at the separate emissions wavelength. Such wavelengths are established by the properties of the selected fluorescent markers. Typically, the emissions are analyzed by an optical scanner, artifacts of the separation are eliminated, and the pattern is interpreted for the characteristics under consideration. Such elimination and interpretation can be conducted manually, or under the control of a computer.

The following examples serve to illustrate certain preferred embodiments and aspects of the present invention and are not to be construed as limiting the scope thereof.

EXPERIMENTAL

In the experimental disclosure which follows, all linear measurements are given in centimeters (cm), millimeters (mm), micrometers ($\mu$m), or nanometers (nm), all electrical potentials are given in volts (V), all weights are given in grams (g), milligrams (mg), micrograms ($\mu$g), nanograms (ng), or picograms (pg), all amounts are given in moles (mol), millimoles (mmol), micromoles ($\mu$mol), nanomoles (nmol), picomoles (pmol), or femtomoles (fmol), all concentrations are given as percent by volume (%), proportion by volume (v:v), molar (M), millimolar (mM), micromolar ($\mu$M), nanomolar (nM), picomolar (pM), femtomolar (fM), or normal (N), all volumes are given in liters (L), milliliters (mL), or microliters ($\mu$L), and radioactivity in counts per minute (cpm), unless otherwise indicated.

The following examples demonstrate the practice of the present invention in selected embodiments.

EXAMPLE 1

1. DNA Isolation and Restriction Enzyme Digestion

Polymerase chain reaction (PCR) is performed in accordance with the protocol described by Smith et al. Briefly, after pre-amplification by multiplex long PCR, each exon or part thereof is amplified in two multiplex groups of 10 and 11 fragments, using primer pairs selected by a TDGS design program (van Orsouw et al., 1998).

2. Electrophoretic Separation

Standard TDGS electrophoresis for hMLH1 using 1-D tube gel electrophoresis followed by a 25–70% UF denaturing gradient slab gel is performed as described by Smith et al. (1998), using the DGGE instrument from C.B.S. Scientific Co. (Del Mar, Calif.). For automated 2-D electrophoresis, the ASG-250 vertical PAGE instrument (C.B.S. Scientific Co.) is used as the foundation. An electrophoresis apparatus of the present invention, consisting of two outer chambers and a middle chamber, is constructed on top of the ASG-250 (FIG. 1).

Figure 5:
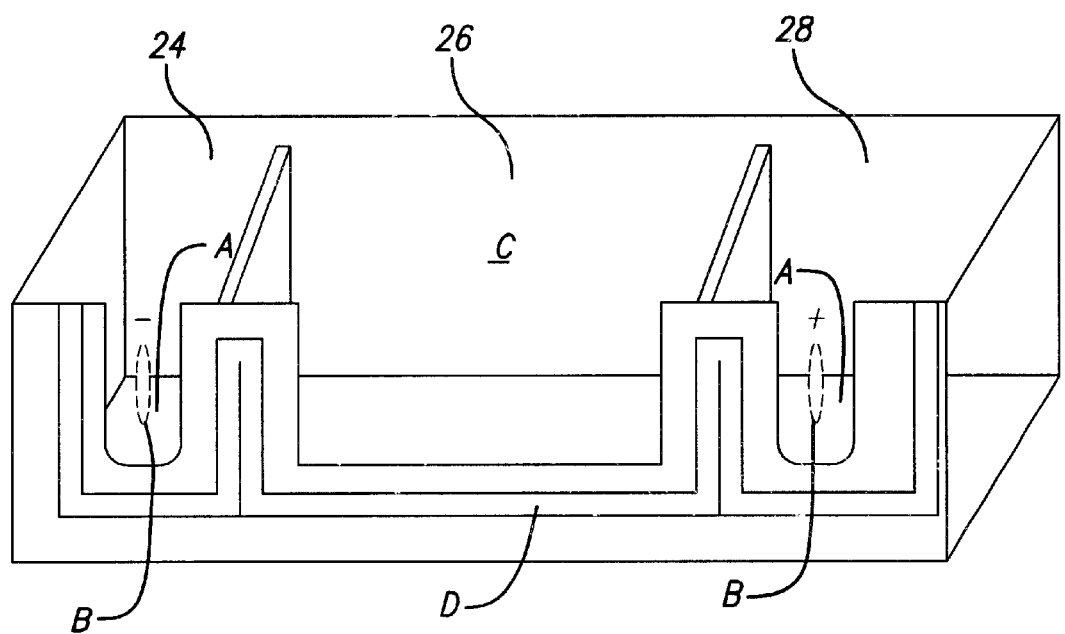
FIG. 5 schematically depicts portions of the glass plate and electrophoresis support components of the assembly of FIGS. 1, 3 and 4.
Figure 5:
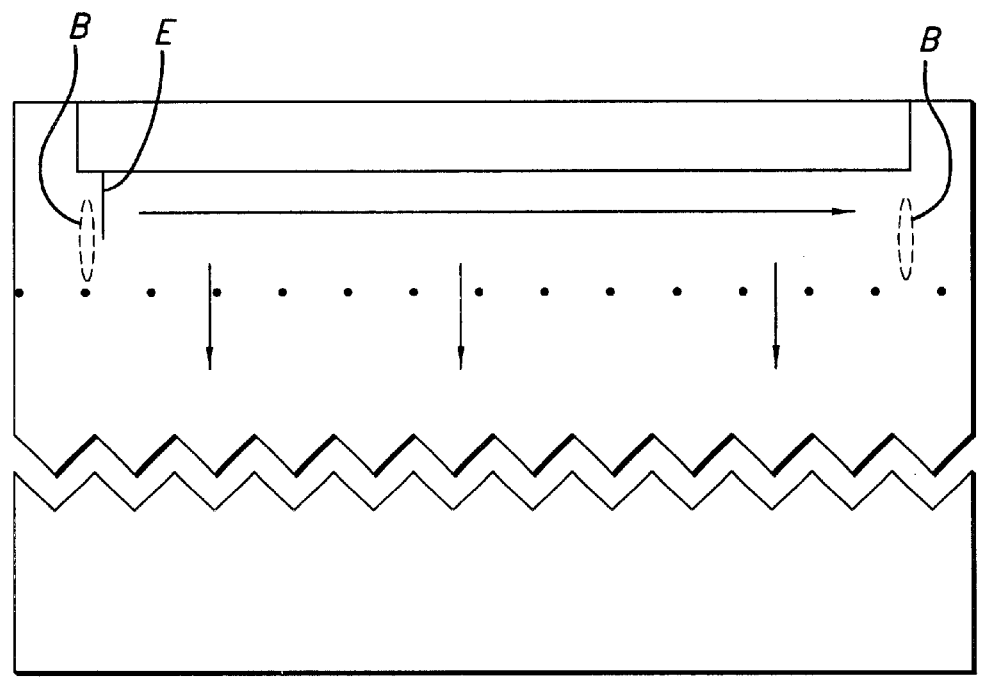

For preparing the gels, pairs of glass plates are used with one notched and one top plate, to form a cassette as depicted in FIG. 2. The notched plate is specifically designed with openings on the sides (FIG. 4) to allow buffer contact with the outer chambers of the top unit FIGS. 2 and 5. Gels are poured using a normal gradient former (Gibco BRL, Gaithersburg, Md.). Boundary gel solutions of 15% UF (urea/formamide), 2% glycerol, 12% acrylamide (37.5:1 acrylamide to bisacrylamide in 0.5xTAE) and 70% UF, 9% glycerol, 6.5% acrylamide, are added to the gradient former after adding TEMED and APS. The gradient is poured no further than about 1 cm below the openings in the notched plate (FIG. 5). After polymerization, a 6.5% polyacrylamide top gel is poured on the gradient gel. A 1-tooth comb (FIG. 2) is inserted into the top gel prior to polymerization to form a well for sample loading. The gel cassette is attached to the instrument using silicone gaskets to prevent leakage from the top buffer chambers alongside the inner (notched) glass plate (FIG. 1). The entire instrument is then placed in a buffer tank (DGGE-4000; C.B.S. Scientific Co.) to keep the temperature at 56° C. (necessary for the second dimension DGGE separation).

After filling the side chambers of the top construction with 0.5xTAE buffer, the sample is loaded and the current turned on for 2.7 hours at 200 V. Upon completion of the size separation, the standard DGGE-4000 pump is attached to the middle reservoir of the 1-D system and turned on, filling it with buffer. The electrodes used for the size separation are detached and the top and bottom electrodes activated according to the standard DGGE-4000 manual. After electrophoresis, the gels are stained with a mixture of equal amounts of SyBr Green I and II in 1xTAE for 15–20 minutes. The resultant separation patterns are then documented under UV illumination using a gel documentation system.

A system is thus provided in which the buffer chambers for the electrophoretic size separation are physically separated from the buffer chambers used in the DGGE separation. This physical separation prevents interaction between the electric fields during the first and second dimension separation and resulted in two different electrophoresis units serving one and the same gel.

The system of the present invention is tested by the comprehensive analysis of the hMLH1 gene by TDGS according to the protocol developed by Smith et al. (1998). The resulting 2-D separation pattern compares favorably with the separation pattern obtained using conventional TDGS, in which the first and second dimension electrophoresis steps are carried out separately in two different gels employing two different instruments. All fragments are detected, and two common polymorphisms in exons 8 and 15 are visualized as easily with the automated format as with the conventional one. However, some differences in the separation patterns should be noted. First, size separation with the present system is compressed as compared with the manual system. This is due to the smaller width of the present apparatus, which can be expanded, if desired. Second, the separation pattern obtained with the present system has a better distribution of spots from the top to the bottom of the gel. This is due to the smaller length of the gel (without the top gel)in the present system, causing a somewhat steeper gradient.

With the discovery of genes associated with specific diseases, accurate, reliable and cost-effective mutation detection systems have become indispensable for genetic epidemiological research and molecular diagnostics. Since the current "gold standard" (nucleotide sequencing) remains an expensive option and the oligonucleotide microarray approach is still immature, cost-effective yet accurate alternatives are in demand. One such alternative is two-dimensional gene scanning (TDGS), a method that combines extensive multiplex PCR with two-dimensional DNA electrophoresis to analyze multiple exons of human disease gene sin parallel (van Orsouw et al., 1996). It has been demonstrated that this technique can be used to screen large numbers of samples for all possible mutations in a number of different genes (van Orsouw and Vijg, 1998). Since DGGE appeared to be close to 100% accurate in identifying sequence variants (Sheffield et al., 1993; Guldburg et al., 1993; Moyret et al., 1994), its application in the second dimension separation of TDGS lends a high degree of sensitivity to the method. The tedious design and optimization, which constitutes the main disadvantage of TDGS (and DGGE in general) has been significantly alleviated by the generation of a computer program to provide complete test designs in minutes (van Orsouw et al., 1998).

The present system differs from previously available systems in numerous ways. The system of the invention is not based on the use of complex pumps and valves to alternately evacuate and fill buffer reservoirs, but on the complete physical separation of the two sets of buffer chambers. This has been accomplished through the use of what can be conceptualized as a separate horizontal electrophoresis unit on top of an existing system for vertical electrophoresis. The necessary contacts between the outer buffer chambers of the top unit and the gel are provided by the additional electrode contacts, such as by the two located channels in the inner glass plate (FIGS. 4 and 5).

Furthermore, in contrast to an earlier design (Mullart et al., 1993), the system presented in accordance with the present invention is not an integral part of the buffer tank needed to maintain a constant elevated temperature in the second dimension (DGGE) separation. The present system can also be operated submerged in a buffer tank, as is demonstrated hereinabove, or applied "dry". In the latter case, the necessary denaturing gradient can be directly generated in the form of a temperature gradient by a plate with several independently controlled temperature isotherms, which can be affixed to each side of the gel cassette. The use of spatially regulated temperature gradients instead of chemical gradients allows more flexibility in the design of a denaturing gradient, obviates the need to pour gradients and permits the use of pre-cast gels (chemical gradients tend to diffuse over time). Finally, the present system can easily be expanded into a multigene unit to run large numbers of 2-D gels in parallel.

The system of the present invention as described herein will permit the rapid and efficient performance of two dimensional gel electrophoretic separations and analysis, while decreasing both the amount and the cost of the labor associated with such assays, and will facilitate standardization of such assays as well. By eliminating the need for manual or robotic manipulations between the first and second dimension separations, as well as permitting the simultaneous performance of both dimensions, the possibility of errors due to tube gel errors is eliminated. Ultimately, the improvements due to the use of the present system, particularly in combination with PCR robots and fluorescent image analysis, should lead to further efficiencies, accuracies, and cost reductions.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

REFERENCES

1. Bronner, C. E., et al. (1994) Mutation in the DNA mismatch repair gene homologue hMLH1 is associated with hereditary non-polyposis colon cancer. *Nature* 368:258–261.

2. Dhanda, R. K., et al. (1998) Critical factors in the performance and cost of two-dimensional gene scanning: RB1 as a model. *BioTechniques* (In Press) 1998.

3. Guldberg, P., et al (1993) Molecular analysis of phenyketonuria in Denmark: 99% of the mutations detected by denaturing gradient gel electrophoresis. *Genomics* 17:141–146.

4. Li, D., et al. (1996) Multiplex co-amplification of 24 retinoblastoma gene exons after pre-amplification by long-distance PCR. *Nucleic Acids Res.* 24:538–539.

5. Moyret, et al. (1994) Relative efficiency of denaturing gradient gel electrophoresis and single strand conformation polymorphism in the detection of mutations in exons 5 to 8 of the p53 gene. *Oncogene* 9:1739–1743.

6. Mullart, E., et al. (1993) Parallel genome analysis by two-dimensional DNA typing. *Nature* 365:469–71.

7. Rhines, D., et al. (1998) Comprehensive mutational scanning of the p53 coding region by two-dimensional gene scanning. *Carcinogenesis*, in press.

8. Sheffield, V. C., et al. (1993) The sensitivity of single-strand conformation polymorphism analysis for the detection of single base substitutions. *Genomics* 16:325–332.

9. Smith, W. M., et al. (1998) Accurate, high throughput "snapshot" detection of hMLH1 mutations by two-dimensional DNA electrophoresis. *Genetic Testing*, in press.

10. Van Orsouw, et al. (1996) Mutational scanning of large genes by extensive PCR multiplexing and two-dimensional electrophoresis: application to the RB1 gene. *Hum Mol Genet* 5:755–761.

11. Van Orsouw, et al. (1998) Rapid design of denaturing gradient-based two-dimensional electrophoretic gene mutational scanning tests. *Nucleic Acids Res.* in press.

12. Van Orsouw, et al. (1998) Design and application of 2-D DGGE-based gene mutational scanning tests. *Genetic Analysis (Biomolecular Engineering)*, in press.

What is claimed is:

1. A two-dimensional gel electrophoresis system comprising means for electrophoretically separating the components of a sample in a slab gel sample well along a first separation path having an axial dimension and a longitudinal dimension extending from said sample well generally along a first dimension in said slab gel and means for electrophoretically separating said separated sample components in a second separation path having an axial dimension and a longitudinal dimension extending from said first separation path generally along a second dimension in said slab gel, wherein said first separation path and said second separation path are established by means for accessing the gel at a plurality of locations intermediate to the boundaries of the gel.

2. A system as recited in claim 1 wherein the axial cross sectional area of said first separation patch is approximately the same as the cross sectional area of said sample well along the entire longitudinal dimension of the first separation path.

3. A system as recited in claim 1 wherein the axial cross sectional area of said second separation path is approximately the same as the longitudinal cross sectional area of said first separation path along the entire length of the second separation path.

4. A system as recited in claim 1 further comprising means for establishing a gradient of at least one electrophoretic parameter across at least one separation path prior to the electrophoretic separation of the components of the sample.

5. A system as recited in claim 4 wherein said electrophoretic parameter is a physical parameter.

6. A system as recited in claim 5 wherein said electrophoretic parameter is temperature.

7. A system as recited in claim 5 wherein said electrophoretic parameter is pore size in the slab gel.

8. A system as recited in claim 4 wherein said electrophoretic parameter is a chemical parameter.

9. A system as recited in claim 8 wherein said electrophoretic parameter is the pH of the slab gel.

10. A system as recited in claim 4 wherein the means for establishing the gradient includes means for establishing a non-linear gradient for said electrophoretic parameter.

11. An apparatus for two-dimensional gel electrophoresis comprising:
(a) means for supporting a substantially rectangular electrophoresis gel, and including therein means for accessing the gel at a plurality of locations intermediate to the boundaries of the gel;
(b) a first electrolyte reservoir located adjacent a first edge of said gel, said reservoir comprising
 (i) a plurality of separate chambers arrayed in alignment with the first edge of the gel and each said chamber configured to permit electrolyte contained within said reservoir to contact at least a portion of the gel adjacent to the first edge of the gel, and
 (ii) at least the two endmost of said chambers each including independent electrode means communicating with the electrolyte contained in said chamber and means for communicating with each said means for accessing the gel, thereby providing means for electrical communication with the said means for accessing the intermediate regions of the gel;
(c) a second electrolyte reservoir located adjacent the opposite edge of said gel configured to permit electrolyte contained within said reservoir to contact at least a portion of said opposite edge of the gel and further comprising
 (i) electrode means communicating with the electrolyte thereby providing means for electrical communication with the said opposite edge of the gel; and
(d) means for providing electrical communication from the electrolyte in said first reservoir to the first edge of said gel.

12. A method for separating a sample into molecular components by utilizing two-dimensional gel electrophoresis comprising:
(a) providing a two-dimensional gel electrophoresis system comprising
 (i) means for electrophoretically separating the components of a sample in a slab gel sample well along a first separation path having an axial dimension and a longitudinal dimension extending from said sample well generally along a first dimension in said slab gel,
 (ii) means for electrophoretically separating said separated sample components in a second separation path having an axial dimension and a longitudinal dimension extending from said first separation path generally along a second dimension in said slab gel;
wherein said first separation path and said second separation path are established by means for accessing the gel at a plurality of locations intermediate to the boundaries of the gel;
(b) loading said sample into said sample well;
(c) imposing an electrical field constrained generally along said first sample path to effect electrophoretic separation of said components of said sample along said first sample path; and
(d) imposing an electrical field generally along said second sample path to effect electrophoretic separation of said components of said sample along said second sample path.

* * * * *